(12) United States Patent
Chandler

(10) Patent No.: US 11,484,386 B2
(45) Date of Patent: Nov. 1, 2022

(54) DENTAL INSTRUMENT WATER SUPPLY FILTER

(71) Applicant: Crosstex International, Inc., Hauppauge, NY (US)

(72) Inventor: James W Chandler, Ashlan, OH (US)

(73) Assignee: Crosstex International, Inc., Hauppauge, NY (US)

( * ) Notice: Subject to any disclaimer, the term of this patent is extended or adjusted under 35 U.S.C. 154(b) by 0 days.

(21) Appl. No.: 17/267,526

(22) PCT Filed: Aug. 28, 2019

(86) PCT No.: PCT/US2019/048465
§ 371 (c)(1),
(2) Date: Feb. 10, 2021

(87) PCT Pub. No.: WO2020/047034
PCT Pub. Date: Mar. 5, 2020

(65) Prior Publication Data
US 2021/0307874 A1     Oct. 7, 2021

Related U.S. Application Data

(60) Provisional application No. 62/724,671, filed on Aug. 30, 2018.

(51) Int. Cl.
*A61C 1/00*     (2006.01)
*C02F 1/00*     (2006.01)
(Continued)

(52) U.S. Cl.
CPC .......... *A61C 1/0076* (2013.01); *A61C 1/0084* (2013.01); *C02F 1/001* (2013.01);
(Continued)

(58) Field of Classification Search
CPC ................ A61C 1/0076; A61C 1/0084; A61C 2204/005; A61M 39/16; C02F 1/001;
(Continued)

(56) References Cited

U.S. PATENT DOCUMENTS

| | | |
|---|---|---|
| 1,637,095 A | 7/1927 | Walters |
| 2,199,258 A * | 4/1940 | Gray ...................... B01D 53/26 422/255 |

(Continued)

OTHER PUBLICATIONS

International Search Report and Written Opinion of the International Searching Authority dated Nov. 14, 2019, of International PCT Application No. PCT/US2019/48465 filed Aug. 28, 2019.
(Continued)

*Primary Examiner* — Terry K Cecil

(57) ABSTRACT

A dental instrument water supply filter includes a hollow cylindrical body which bounds an interior area. The interior area houses a plurality of iodinated resin particles. A pair of water permeable discs are positioned in the interior area of the body at opposed axial ends. End caps close the interior area of the body at the respective opposed ends, and each end cap includes a respective removable fluid fitting. Water that is used in connection with the operation of a dental instrument is passed through the filter. The filter provides filtration and reduces microorganisms in the water that is passed therethrough and also releases ions into the water that are effective to reduce the growth of contaminants in the water lines to the instrument.

17 Claims, 12 Drawing Sheets

(51) Int. Cl.
*C02F 1/76* (2006.01)
*C02F 103/02* (2006.01)

(52) U.S. Cl.
CPC ........ *C02F 1/766* (2013.01); *A61C 2204/005* (2013.01); *C02F 2103/026* (2013.01); *C02F 2201/004* (2013.01); *C02F 2201/006* (2013.01); *C02F 2209/008* (2013.01); *C02F 2209/445* (2013.01); *C02F 2303/04* (2013.01)

(58) Field of Classification Search
CPC ................ C02F 1/766; C02F 2103/026; C02F 2201/004; C02F 2201/006; C02F 2209/008; C02F 2209/445; C02F 2303/04
See application file for complete search history.

(56) References Cited

U.S. PATENT DOCUMENTS

| | | | |
|---|---|---|---|
| 2,595,445 A * | 5/1952 | Bottum | F25B 43/003 210/287 |
| 3,490,580 A | 1/1970 | Brumfield et al. | |
| 3,788,476 A | 1/1974 | Othmer | |
| 4,238,477 A | 12/1980 | Fina et al. | |
| 4,741,697 A | 5/1988 | Herbison | |
| 5,073,382 A | 12/1991 | Antelman | |
| 5,176,836 A * | 1/1993 | Sauer | G05D 21/02 210/764 |
| 5,223,149 A | 6/1993 | Antelman | |
| 5,230,624 A | 7/1993 | Wolf et al. | |
| D351,892 S | 10/1994 | Wolf et al. | |
| 5,370,534 A | 12/1994 | Wolf et al. | |
| 5,401,399 A | 3/1995 | Magnusson et al. | |
| 5,556,279 A | 9/1996 | Wolf et al. | |
| 5,882,507 A | 3/1999 | Tanner et al. | |
| 6,254,894 B1 | 7/2001 | Denkewicz, Jr. et al. | |
| 6,325,929 B1 | 12/2001 | Bassett | |
| 6,562,241 B1 | 5/2003 | Gritton et al. | |
| 6,616,197 B2 | 9/2003 | Sampson | |
| 6,863,905 B1 | 3/2005 | Shanbrom | |
| 7,250,111 B2 | 7/2007 | Doxey et al. | |
| 7,329,385 B1 | 2/2008 | Radicone et al. | |
| 7,481,917 B2 | 1/2009 | Ikeyama et al. | |
| 7,491,330 B2 | 2/2009 | Harvey | |
| 7,704,399 B2 | 4/2010 | Condit | |
| 8,252,185 B2 | 8/2012 | Rajan et al. | |
| 9,750,834 B1 | 9/2017 | Hammarback | |
| 2005/0194317 A1 * | 9/2005 | Ikeyama | B01D 63/10 210/321.74 |
| 2006/0208397 A1 | 9/2006 | Ichikawa | |
| 2009/0225808 A1 | 9/2009 | Dileo | |
| 2017/0034844 A1 | 12/2017 | Hammarback | |

OTHER PUBLICATIONS

International Preliminary Report on Patentability issued in PCT/US2019/048465, dated Mar. 11, 2021.

* cited by examiner

DENTAL INSTRUMENT WATER SUPPLY FILTER

CROSS REFERENCE TO RELATED APPLICATIONS

This application claims priority to U.S. Provisional Patent Application Ser. No. 62/724,671 filed Aug. 30, 2018. This application is incorporated herein by reference, in its entirety.

TECHNICAL FIELD

Exemplary embodiments relate to dental equipment. Particular exemplary embodiments relate to a water supply filter for use with dental instruments.

BACKGROUND

Water is frequently used in connection with the operation of dental equipment and dental procedures. It is desirable to have the water that is used in connection with such dental equipment not be contaminated with bacteria, viruses, molds or other harmful materials.

Water that is supplied to dental instruments must travel from a source through lines to reach the dental instruments. Even if the water from the source is free of harmful materials it is possible for the lines to become contaminated with harmful materials. Various approaches can be taken to disinfect the water lines that lead from the water source to the dental instrument or to otherwise minimize the risk of contamination of the water and the lines.

Techniques for minimizing the risk of contamination in water lines that supply dental instruments may benefit from improvements.

SUMMARY

Exemplary embodiments include a dental instrument water supply filter that is configured to be installed in fluid connection with water lines through which water is passed to a dental instrument. The exemplary filter includes iodinated resin particles that are operative to produce ions in the water that passes through the filter. The ions reduce the risk of the growth of bacteria, viruses, molds or other harmful materials in the lines that are fluidly connected downstream of the filter. In exemplary arrangements the filter is suitable for installation in fluid communication with numerous types of dental instruments.

Further features and advantages of exemplary embodiments will be made apparent in the following Detailed Description and the appended claims.

DETAILED DESCRIPTION

Figure 1:
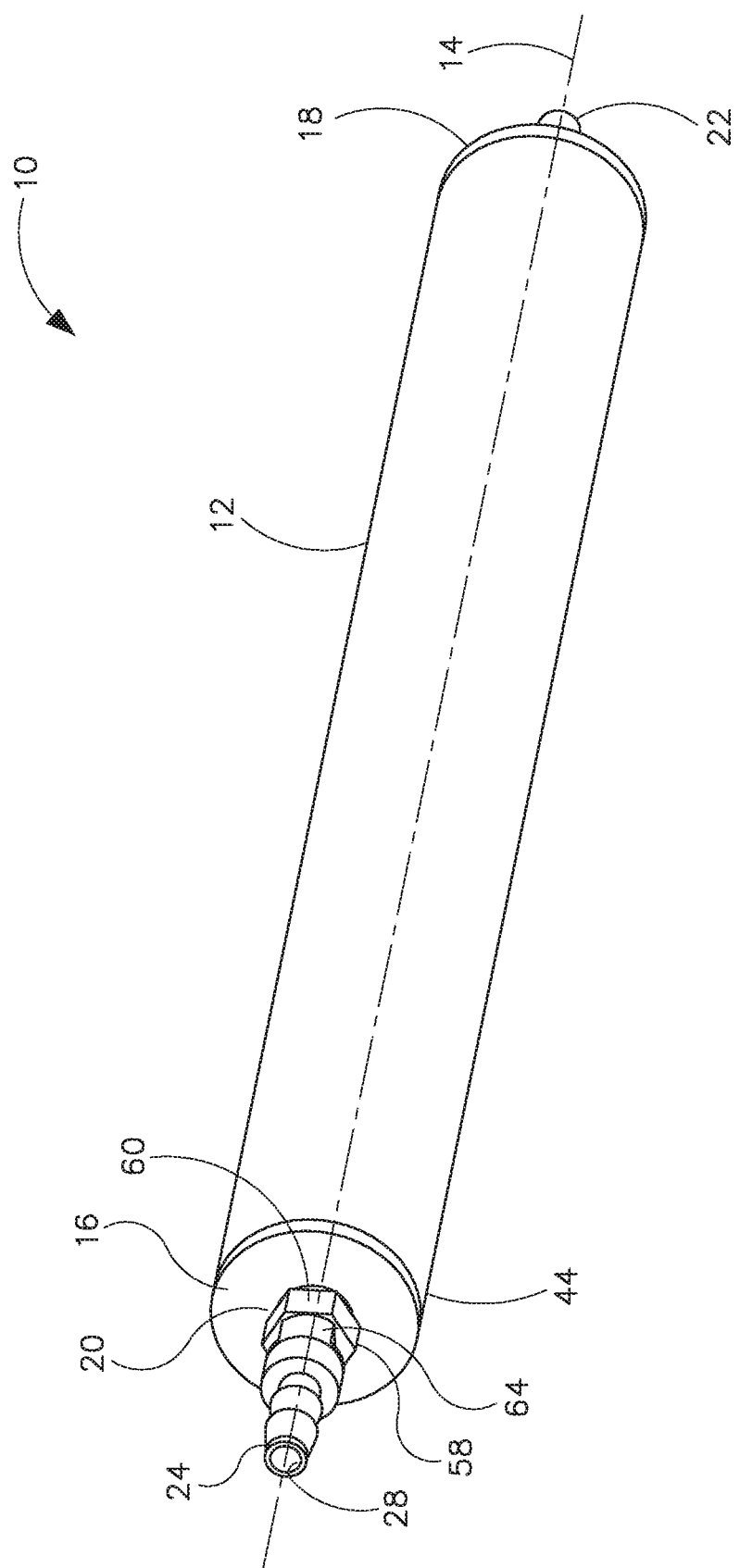
FIG. 1 is a front top perspective view of an exemplary dental instrument water supply filter.
Figure 2:
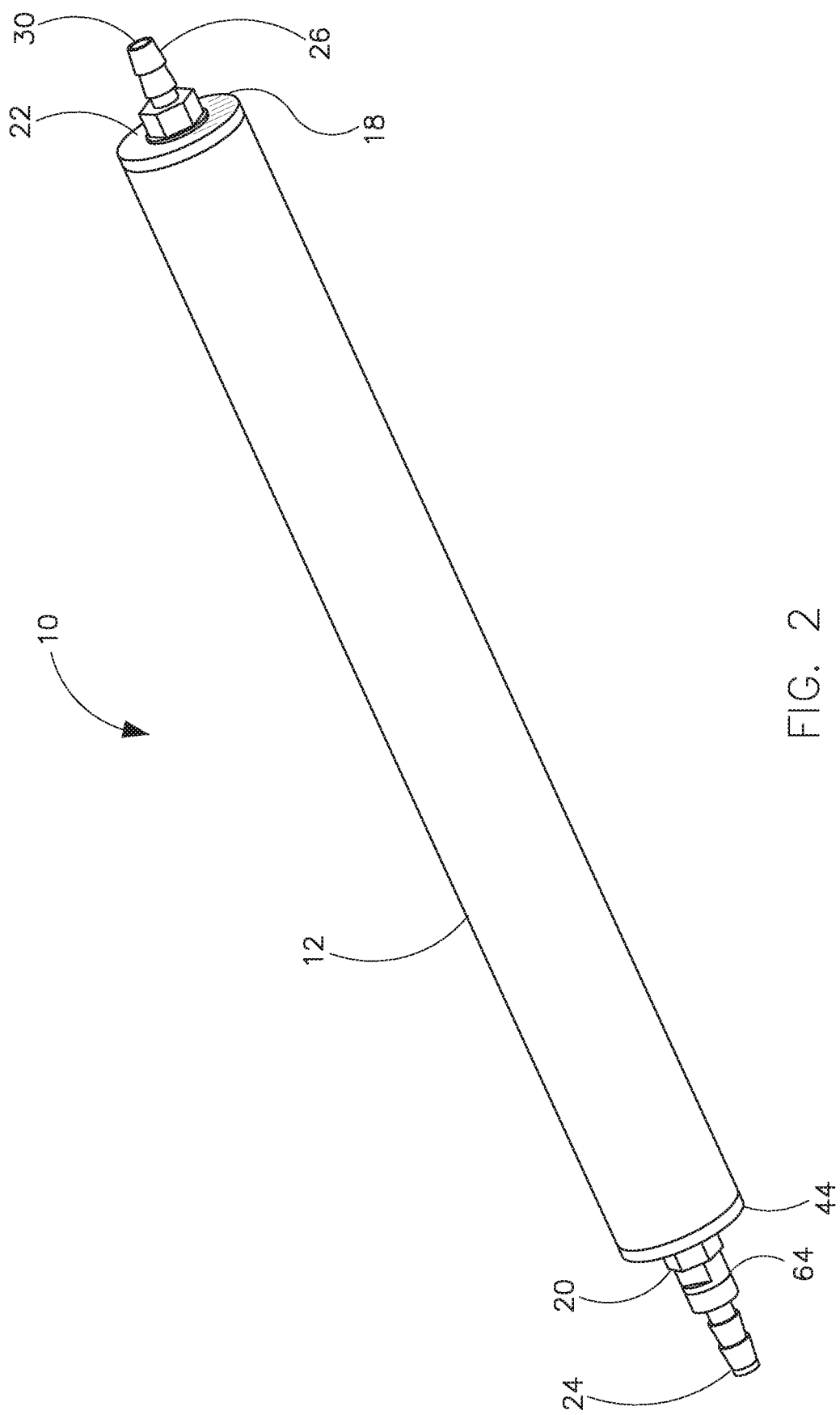
FIG. 2 is a rear bottom perspective view of the exemplary dental instrument water supply filter.

Referring now to the drawings and particularly to FIG. 1 there is shown therein an exemplary dental instrument water supply filter generally indicated 10. The exemplary filter includes an elongated hollow cylindrical body 12 that extends along a longitudinal axis 14.

The exemplary filter includes a front end cap 16 at a first axial end of body 12, and a rear end cap 18 at an opposed second axial end of the body. A fitting 20 extends axially outward from front end cap 16. A fitting 22 extends axially outward from rear end cap 18. Exemplary fitting 20 includes a barbed fitting end 24 that extends axially outward and away from the body 12. Exemplary fitting 22 includes a barbed fitting end 26 that extends axially outward and away from the body 12. Exemplary fittings 20 and 22 include respective fluid openings 28 and 30 that extend axially therethrough. The exemplary barbed fitting ends of the fittings are configured to releasably engage the respective fitting in fluid tight engagement with an adjacent flexible water line such as a tube. Of course it should be understood that this connection construction is exemplary and other embodiments other fluid connection approaches may be used.

Figure 3:
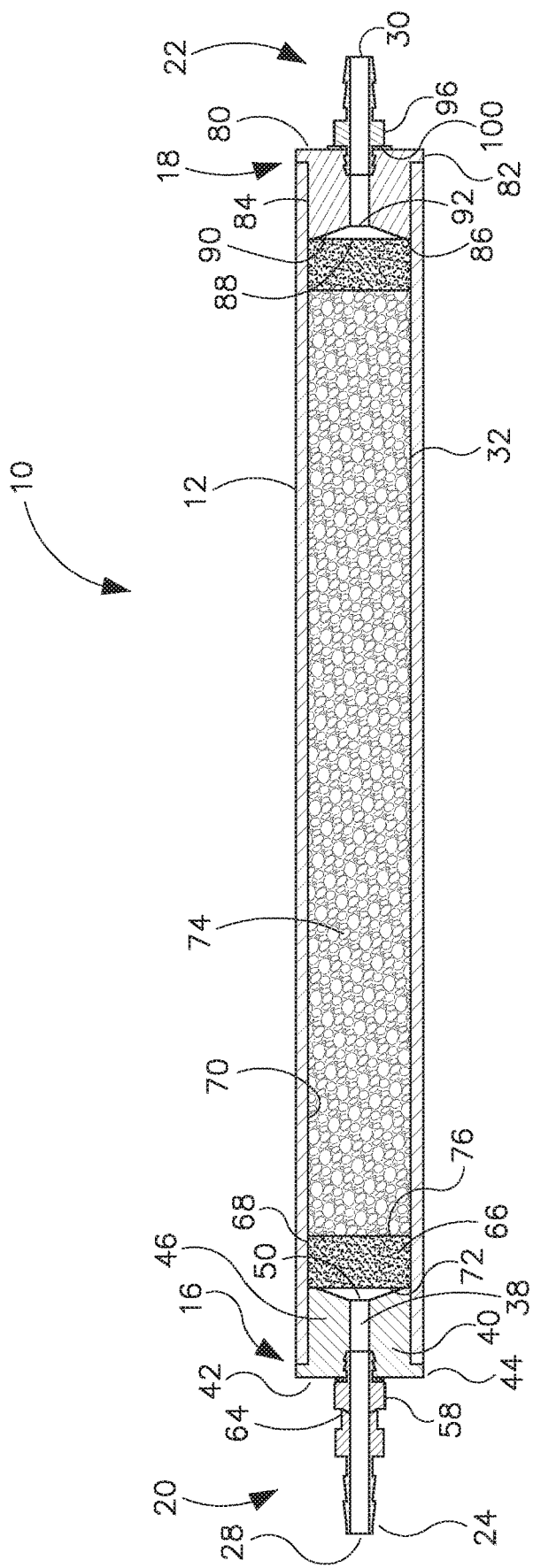
FIG. 3 is a transverse cross-sectional view of the exemplary filter.
Figure 4:
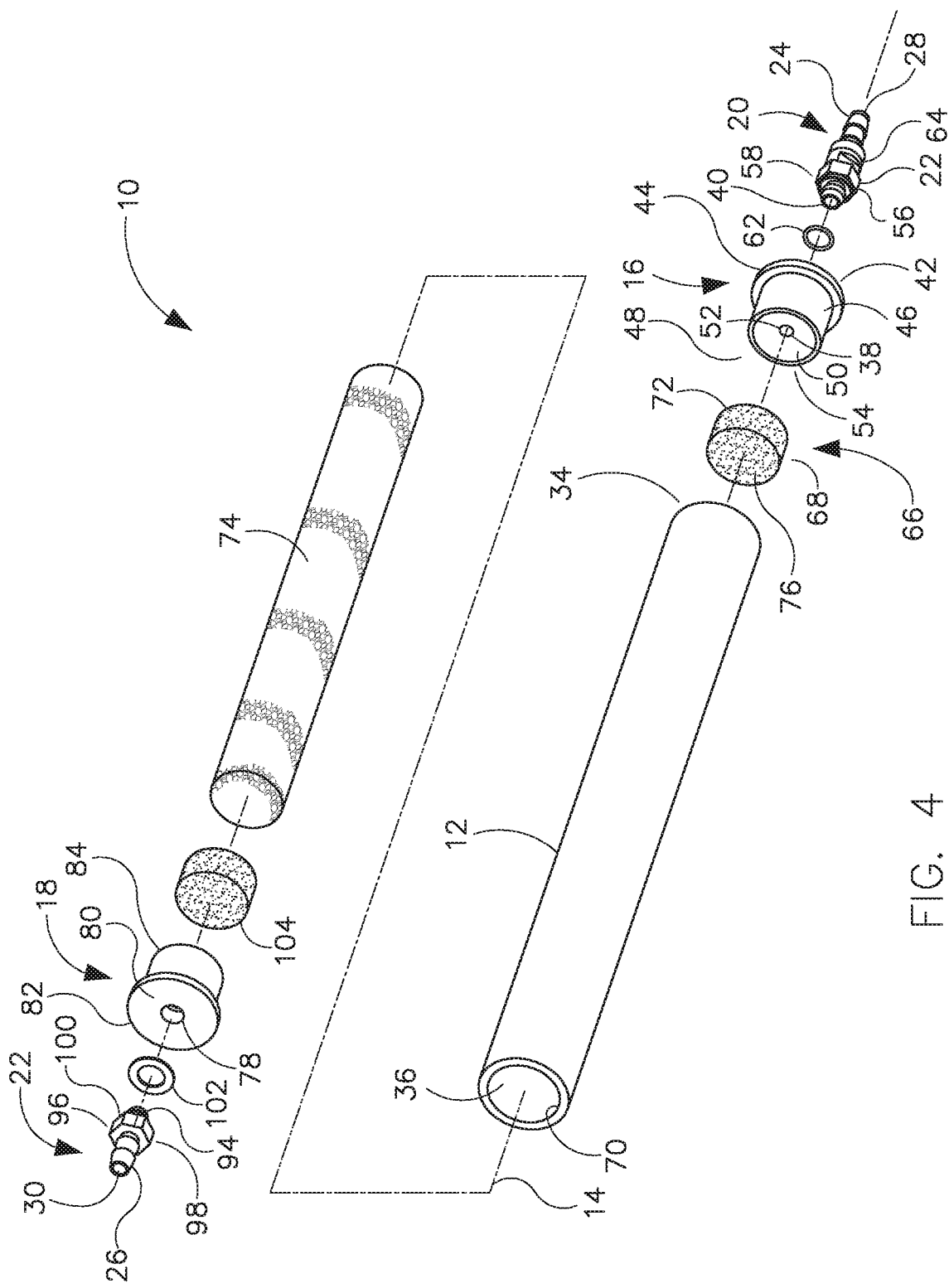
FIG. 4 is an exploded perspective view of the exemplary filter.

As shown in FIGS. 3 and 4 the body 12 of the exemplary dental instrument water supply filter bounds an interior area 32. The body further includes a first axial end opening 34 adjacent to the first axial end of the filter body, and a second axial end opening 36 at the opposed second axial end of the filter body. The exemplary axial end openings are circular openings; however it should be understood that in other embodiments other opening configurations may be used.

The exemplary front end cap 16 includes an axially aligned end cap opening 38. Opening 38 is at least partially threaded and configured to receive a threaded fitting end 40 of fitting 20 therein. In the exemplary arrangement this configuration enables fitting 28 to be releasably engaged with front end cap 16.

In the exemplary arrangement front end cap 16 includes a flat circular outer face 42. The end cap opening 38 extends through the flat circular outer face 42. In the exemplary arrangement the circular outer face extends radially outward and terminates at a flange portion 44. The exemplary flange portion 44 is configured to be in abutting relation with the body 12 adjacent to the first axial end opening 34.

The exemplary end cap 16 further includes a plug portion 46. The exemplary plug portion 46 extends in the interior area 32 of the body 12. The plug portion 46 of exemplary end cap 16 extends inwardly from the first axial end opening 34. The axially inward position of the plug portion within the body interior area is determined by engagement of the flange portion 44 with the circular face of the cylindrical body bounding the axial end opening 34. In the assembled condition of the filter the plug portion 46 is secured to the body 12 by an adhesive or other suitable fastening methods. Of course it should be understood that this configuration is exemplary and in other embodiments other approaches may be used.

The exemplary end cap 16 further includes an inner face 48. The inner face is axially opposed of the outer face 42. The exemplary inner face 48 includes an axial recess 50. The exemplary recess 50 has a hemispherical or frustoconical shape. An inner end 52 of end cap opening 38 extends through inner face 48. In the exemplary arrangement the recess 50 extends in annular surrounding relation of the inner end 52 of the end cap opening. In the exemplary arrangement an annular land 54 extends in surrounding relation of the recess 50. In the exemplary arrangement the annular land comprises a generally radially extending surface and is axially disposed inwardly in the interior area of the filter body from the inner end 52 of the end cap opening 38 for reasons that are later discussed.

In the exemplary arrangement fitting 20 includes a flat fitting face 56. The flat fitting face 56 extends perpendicular to the axis 14. The exemplary flat fitting face 56 axially bounds a radially enlarged portion 58 of the fitting 20. The exemplary radially enlarged portion 58 includes wrench flats 60 on the external surface thereof. The exemplary wrench flats facilitate engagement of the fitting with a wrench or other tool that is suitable for engaging or disengaging the fitting 20 and the end cap 16 through rotational engagement of the threaded fitting end 40 with the threaded end cap opening 38.

In the exemplary arrangement an annular resilient seal 62 is configured to extend in surrounding relation of the outer end of end cap opening 38 on the flat circular outer face 42 of end cap 16. In the assembled condition of the filter, the seal 62 also extends in surrounding relation of the threaded fitting end 40 of fitting 20. The seal 62 is positioned so as to extend in axially sandwiched relation between the flat circular outer face 42 of end cap 16 and the flat fitting face 56 of fitting 20. Seal 62 helps to assure that fitting 20 is engaged with the end cap 16 and the fitting in fluid tight relation. Of course it should be understood that this configuration is exemplary and in other embodiments other arrangements may be used.

In the exemplary embodiment, fitting 20 includes a fluid tight swivel joint 64. The exemplary fluid tight swivel joint is rotatable so that the barbed fitting end 24 may rotate relative to the threaded fitting end 40 of the fitting 20. In the exemplary arrangement the fluid tight rotatable swivel joint can facilitate the installation of the exemplary filter 10 in a water line that is required to rotate and twist during operation of the associated dental instrument. Of course it should be understood that this configuration is exemplary and in other embodiments other arrangements and fitting configurations may be used.

In the exemplary arrangement a generally rigid water permeable disc 66 is positioned in axially adjacent abutting engagement with the plug portion 46 of the end cap 16. In the exemplary embodiment the water permeable disc 66 comprises a disc shaped piece that has an outer annular periphery that closely conforms in size to the inside diameter of the interior area 32 of the filter body 12. Disc 66 is comprised of material that has very small porous passages that enables water molecules to pass therethrough while preventing the passage of particulate material. In exemplary arrangements the water permeable disc may be comprised of agglomeration of formed particles and/or fibers of plastic or metals that will not have an adverse effect on the quality of the water that passes therethrough. The exemplary disc 66 is configured to have a pore size which will prevent the flow of particulates while enabling water to flow therethrough at a suitable flow rate.

In the exemplary arrangement the water permeable disc 66 is sufficiently rigid and sized so that water or other material cannot pass through the interface of the annular disc outer peripheral surface 68 and the annular interior wall 70 that bounds the interior area 32 of the body 12. Further in the exemplary arrangement disc 66 includes a circular generally planar outer face 72. In the assembled condition of the filter the radially outward portions of the disc outer face 72 are in abutting engagement with the annular land 54 on the plug portion 46 of end cap 16. This exemplary configuration enables the recess 50 to be exposed and open to the majority of the surface area of the disc outer face 72. This facilitates flow through the water permeable disc 66 by having more area of the outer face of the disc exposed to the water which is delivered through the end cap opening 38.

Of course it should be understood that this configuration of the water permeable disc and the end cap is exemplary and other embodiments other approaches and constructions may be used to facilitate the flow through the disc material which serves to filter the water which passes therethrough while preventing water from bypassing the filter material. Further it should be understood that while the description of the end cap 16 and the fitting 20 has been presented as providing the incoming flow of water to the filter body, the filter may also be used in a manner which provides for the outflow of treated water from the end cap 16 and the fitting 20 as later discussed.

In the exemplary arrangement the body interior area 32 is filled with a plurality of iodinated resin particles generally indicated 74. The resin particles are in contact with a circular disc inner face 76 of water permeable disc 66. In the exemplary arrangement the iodinated resin particles are sized sufficiently small to facilitate the release of ions to the water which passes therethrough for purposes of providing disinfecting properties to the water, while at the same time the particles are sufficiently large so that they are prevented from passing through or around the periphery of the water permeable disc 66. The exemplary iodinated resin particles are also configured to be packed within the interior area in a manner that is sufficiently porous so as to enable the desired level of water flow to pass therethrough, as well as to provide for suitable duration of contact of the water with the particles so as to disinfect the water and to impart the desired level of iodine ions in the water that passes out of the filter so as to prevent the growth of microorganisms in the connected water lines and other structures. This may be accomplished chemically in a manner like that discussed in U.S. Pat. No. 5,176,836 which is incorporated herein by reference in its entirety. Of course it should be understood that this approach is exemplary and in other embodiments other or additional materials may be utilized for purposes of providing filtering and disinfecting properties and/or to prevent the growth of microorganisms in the water that is passed through the filter.

In the exemplary embodiment structures similar to those described at the front end of the filter including end cap 16 and fitting 20, are included at the opposed end of the filter body that includes end cap 18 and fitting 22. In the exemplary arrangement end cap 18 includes a partially threaded end cap opening 78 that is configured in a manner similar to end cap opening 38. End cap 18 also includes a flat circular outer face 80 similar to flat circular outer face 42 of end cap 16. End cap opening 78 extends through the flat circular outer face 42. The flat circular outer face 80 terminates in a flange portion 82 that is sized to abuttingly engage the annular face of body 12 that bounds the axial end opening 36.

End cap 18 further includes a plug portion 84. Plug portion 84 is similar to plug portion 46 of end cap 16, and is sized to extend in the interior area 32 of the body in close-fitting relation with the annular interior wall 70 adjacent to axial end opening 36. Plug portion 84, similar to plug portion 46, includes an inner face 86 which includes a recess 88 which is bounded radially outwardly by an annular land 90. Also similar to the configuration of end cap 16, the end cap opening 78 has an inner end 92. A hemispherical or frustoconical shaped recess 88 extends in annular surrounding relation of the inner end 92. In the exemplary embodiment the plug portion 84 is secured to the body 12 through an adhesive or other suitable securing methods.

In the exemplary arrangement fitting 22 is similar to fitting 20 except that fitting 22 does not include a fluid tight rotatable swivel joint. This is done in the exemplary arrangement because in most mounting configurations of the filter body only one swivel joint is needed to enable desired rotational movement of the filter body. However in other exemplary embodiments the fittings at both ends of the filter may include fluid tight rotatable swivel joints, or in other embodiments no swivel joints may be included in the fittings.

Exemplary fitting 22 includes a threaded fitting end 94 at an axial end of the fitting opposed of the barbed fitting end 26. The threaded fitting end is configured to releasably threadably engage in end cap opening 78. Fitting 22 further includes a radially enlarged portion 96 that includes a plurality of wrench flats 98 thereon to facilitate engagement with a wrench or other suitable tool used for rotationally engaging and disengaging the fitting 22 and the end cap 18. Fitting 22 further includes a flat radially extending fitting face 100 that axially inwardly bounds the radially enlarged portion 96.

A resilient seal 102 which in the exemplary arrangement is similar to seal 62, is configured to extend in surrounding relation of the threaded fitting end 94 of fitting 22. Seal 102 is also configured to extend in axially sandwiched relation between the flat circular outer face 80 of end cap 18 and the flat fitting face 100 of fitting 22. The seal in the exemplary arrangement helps to assure that the fitting 22 is engaged with the end cap 18 in fluid tight relation.

A water permeable disc 104 is axially positioned between the plug portion 84 of end cap 18 and the iodinated resin particles 74. Water permeable disc 104 in the exemplary arrangement, has the same configuration as water permeable disc 66. In the assembled condition of the filter 10 the disc 104 serves to maintain the resin particles disposed from the end cap 18 and the end cap opening 78 therein. The disc further serves to filter and capture particulates in the water that passes therethrough so as to provide a filtration function.

The exemplary disc 104 further includes a flat circular face which is engaged with the annular land 90 of the plug portion 84. As previously discussed, this configuration in the exemplary embodiment causes the inner end of the end cap opening to be axially disposed from the circular face of the immediately adjacent water permeable disc and enables most of the surface area of the circular face of disc 104 to be exposed to the recess 88 so as to facilitate the flow of water therethrough.

It should be understood that although the components used at both ends of the exemplary filter are similar, in other exemplary arrangements the ends of the filter may include different structures. These different structures may be used to achieve different mounting configurations or other desired flow properties which may be useful in particular applications of particular embodiments. Further it should be understood that while the exemplary embodiment is described in connection with barbed fitting connectors, other embodiments may include other types of fluid connectors at one or both ends of the filter. These may include for example, compression fittings, push to connect fittings, lure type fittings or other types of fluid connectors.

In the exemplary arrangement the filter 10 is usable in supplying water through lines or other fluid conduits (which for purposes hereof are referred to as lines) to dental instruments (which are alternatively referred to herein as tools) which use the delivered water in connection with the operation of such instruments. Examples of such dental instruments include spray nozzles which are used in dental procedures to selectively deliver water into the mouth of a patient. Other examples of dental instruments include devices such as ultrasonic cleaning devices that may utilize a water flow in connection with the removal of debris from the site of the cleaning activity. Other examples of dental instruments may include drilling, grinding, brushing, polishing or other devices that utilize water as a cooling, rinsing or lubricating material in connection with the operation of the instrument. Exemplary dental instruments may be of the types operated to perform functions within the mouth of the patient or may be of the types used externally of the patient for purposes of conducting activities in connection with items that are placed in the mouth of the patient such as for forming, cleaning or modifying retainers, dentures or implants. Instruments may also include devices that are used to preserve the cleanliness of other dental devices and instruments. It should be understood that many different types of dental instruments and tools may be utilized in connection with exemplary embodiments of the dental instrument water supply filters described herein.

Figure 5:
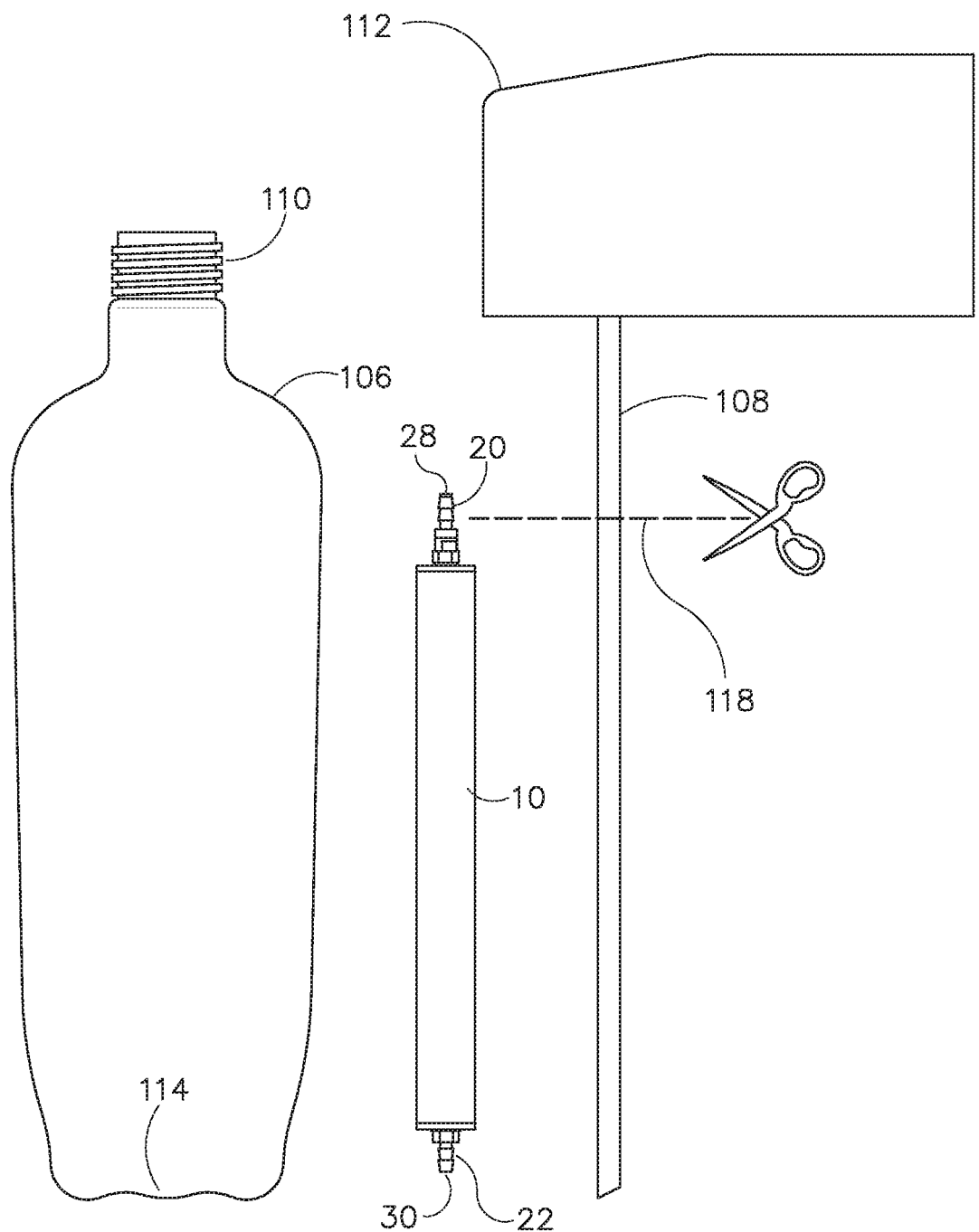
FIG. 5 is a side view showing the exemplary filter and an exemplary water holding bottle in which the filter may be installed.

FIG. 5 shows an exemplary arrangement in which the exemplary dental instrument water supply filter 10 may be used in a system that supplies water to one or more dental instruments. In the exemplary arrangement a water holding bottle 106 is configured to hold water that is supplied to the dental instrument through a vertically extending flexible line which is referred to as tube 108. The exemplary bottle includes a threaded upper end 110 that is configured to releasably attach the bottle and a bottle mounting head 112. In this exemplary arrangement prior to the installation of the filter 10 in connection with the water supply bottle, the tube 108 extends vertically in the bottle to somewhat above a closed bottle bottom end 114. Thus as can be appreciated, when the water holding bottle 106 is filled with water and mounted to the head, the tube 108 extends downward within the bottle and in the water therein to adjacent the closed bottom end 114. Thus in this exemplary arrangement prior to the installation of the filter, water may be drawn from the interior area 116 of the water holding bottle 106 until the water level has dropped to a point where virtually no water remains.

In this exemplary arrangement when it is desired to implement the exemplary water supply filter, the water holding bottle is disengaged from the head 112. The tube 108 is then cut as represented by line 118. The vertically extending flexible tube 108 can then have the lower severed end portion thereof discarded.

With the tube 108 having been shortened a desired amount, a fitting of the filter 10 is then fluidly connected to the tube 108. In the exemplary arrangement shown the barbed fitting end 24 of fitting 20 is connected via a press fit to the tube 108. It should be understood however that in this arrangement the other fitting 22 of the filter could be connected directly to the tube 108 instead of fitting 20.

Figure 6:
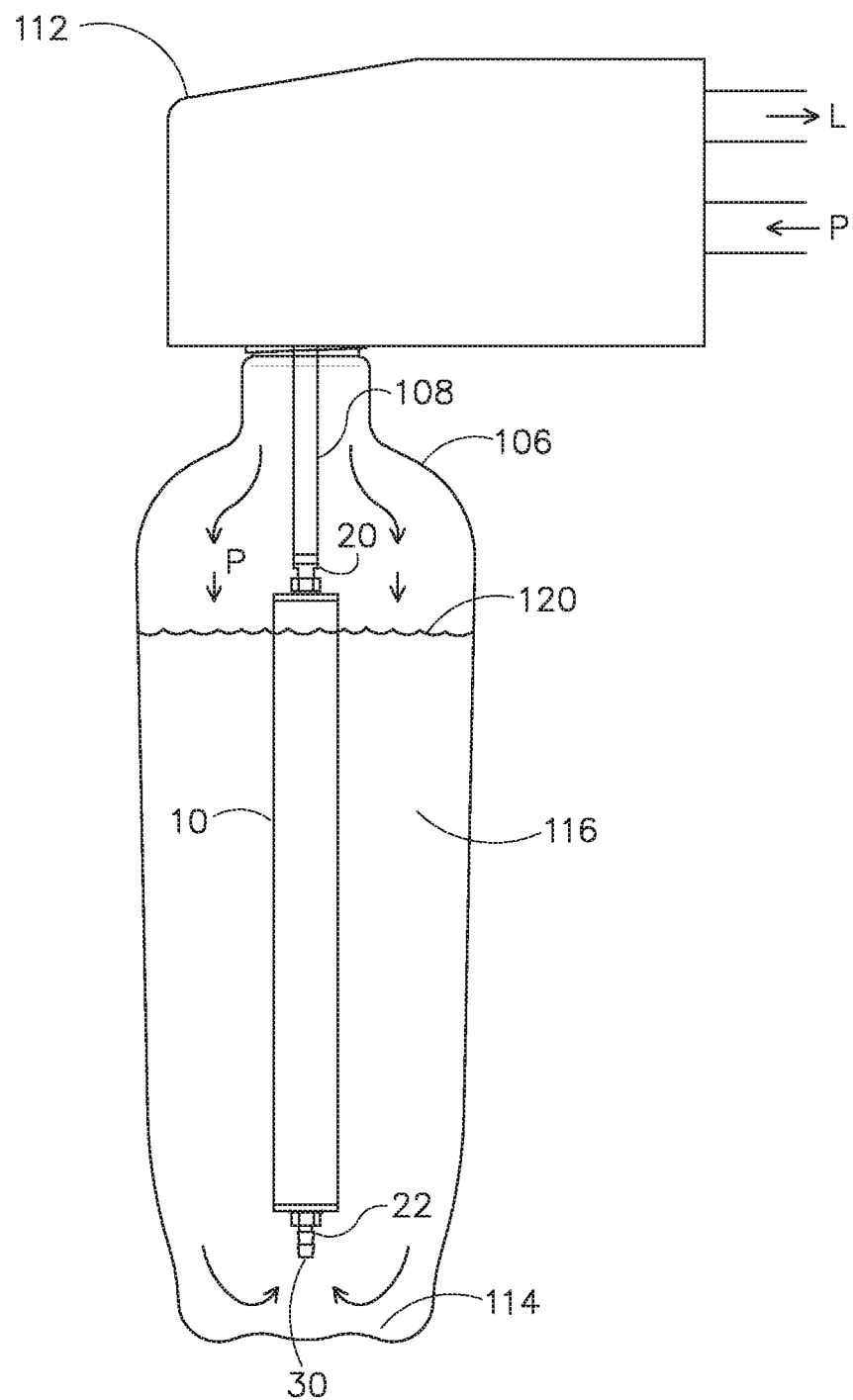
FIG. 6 is a side view showing the exemplary filter installed in a first configuration within the water holding bottle.

Once the filter 10 is connected to the tube 108 the water holding bottle 106 is filled with water and connected to the head 112 as shown in FIG. 6. In this exemplary configuration the fluid opening 30 in fitting 22 is disposed vertically above the closed bottom end 114 a vertical distance generally comparable to that of the original tube 108 prior to being shortened.

In this exemplary arrangement water is caused to move from the bottle interior area 116 by the application of air pressure that is elevated somewhat above ambient air pressure, through the mounting head into the upper area of the bottle interior 116. This is represented in FIG. 6 by the Arrows P. The air pressure acting on the surface of the water 120 in the bottle interior area is operative to cause the water therein to the moved through the fluid opening 30 in fitting 22. The water moves upwardly through the filter 10 and out of fluid opening 28 in fitting 20. The water that is passed upwardly through the filter 10 passes through the tube 108 and out of the head 112. This is represented by Arrow L.

Figure 7:
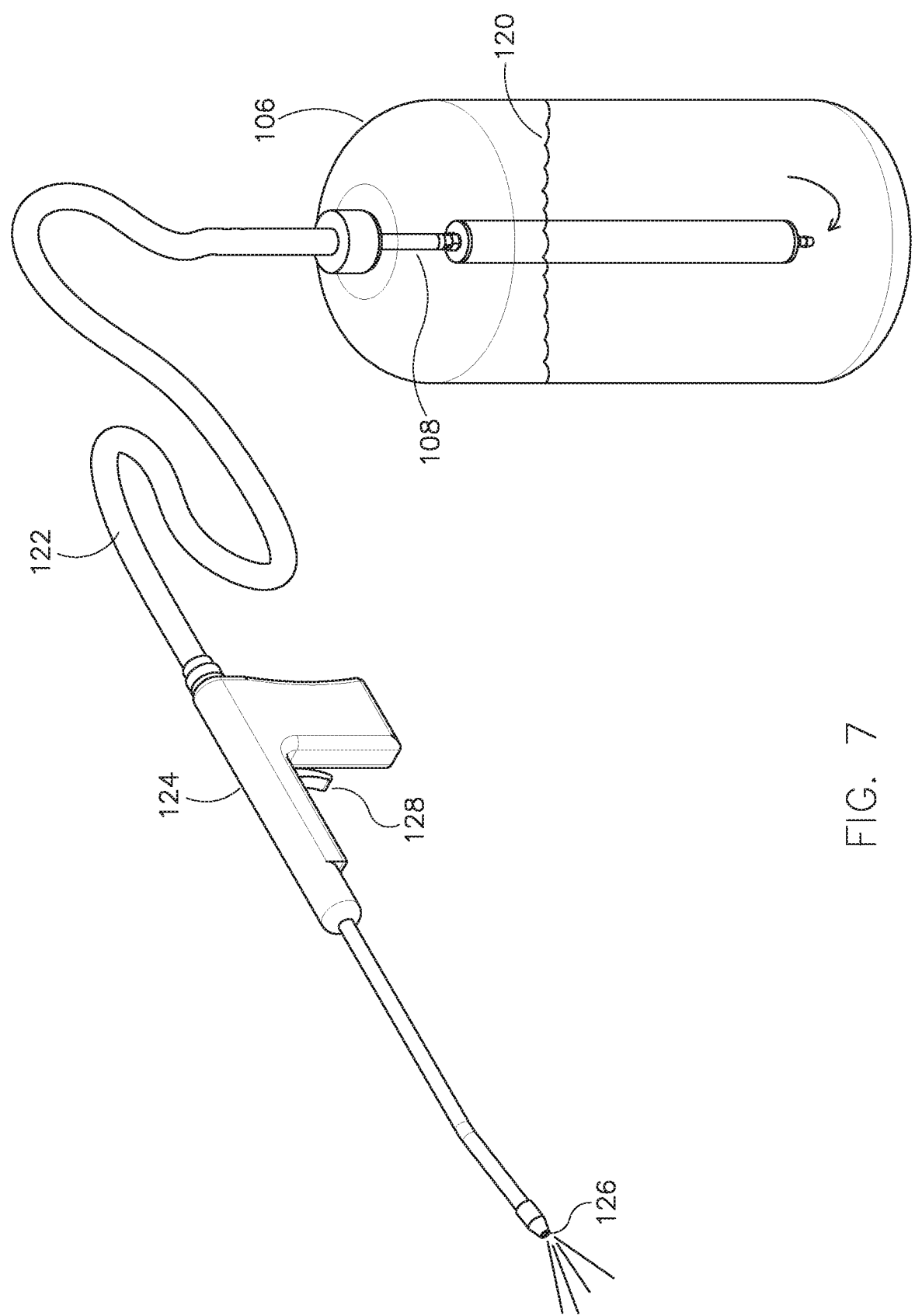
FIG. 7 is a perspective view showing the filter within the water holding bottle and supplying water to a dental instrument.

FIG. 7 shows schematically an exemplary arrangement in which water from the water holding bottle 106 is passed through tubing or other suitable conduit 122 to a dental instrument 124. In the exemplary arrangement the dental instrument shown is represented as a manually actuatable water spray device. This device may be used to selectively spray water delivered from the water holding bottle into a selected area within the mouth of the patient that is undergoing a dental procedure. The exemplary dental instrument includes a water outlet 126 from which the water can be selectively sprayed. The exemplary instrument 124 further includes a finger actuated trigger 128 which can be manually actuated by the dental professional for purposes of controlling the flow of water from the water outlet. Of course it should be understood that this dental instrument and arrangement is exemplary and other embodiments other arrangements may be used.

Figure 8:
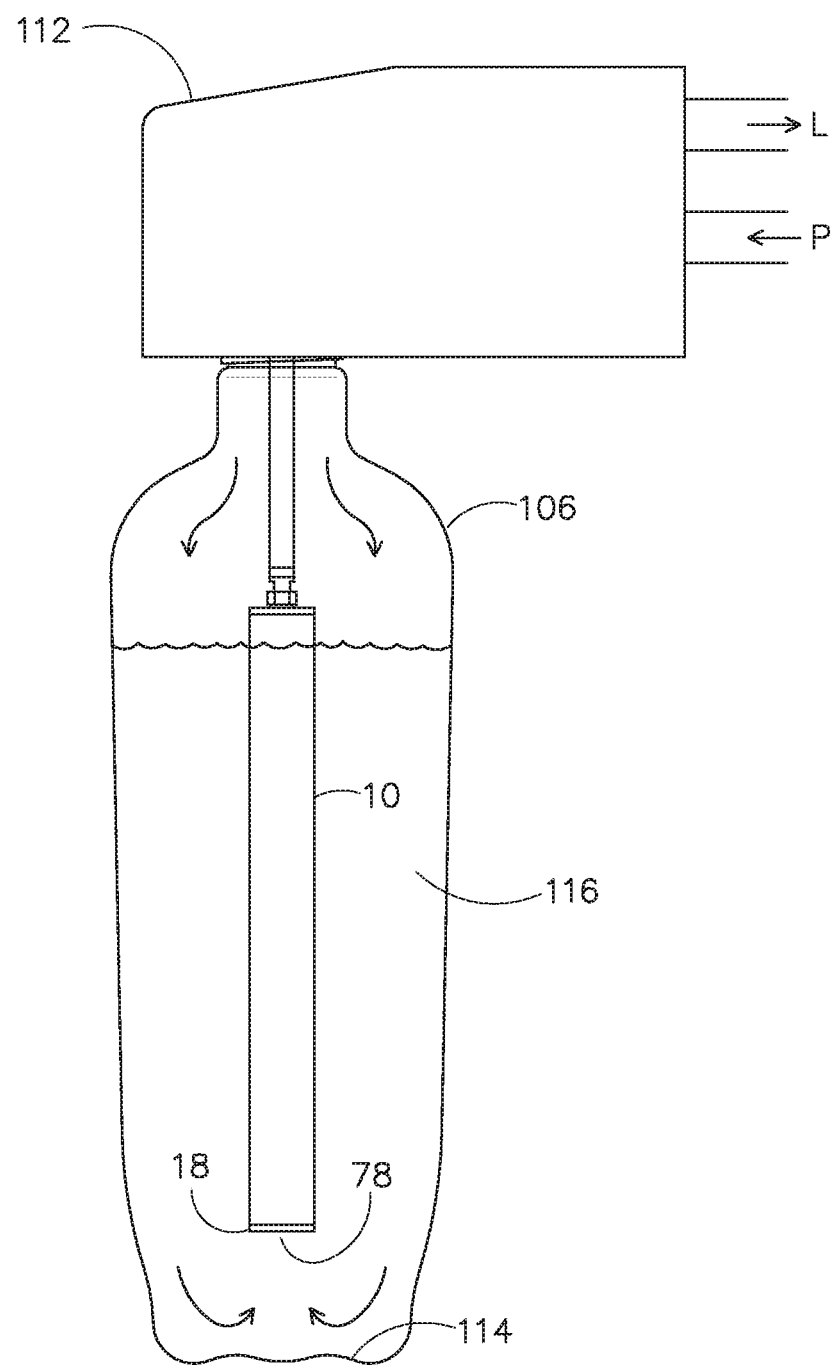
FIG. 8 is a side view showing the exemplary filter installed in a second configuration within a water holding bottle.

FIG. 8 shows an alternative configuration for installation of the exemplary dental instrument water supply filter 10 in a water holding bottle such as bottle 106. In this exemplary mounting arrangement, the fitting 22 and associated seal 102 have been removed from the end cap 18 of the filter 10 prior to installation of the filter in the interior area of the bottle. In this mounting configuration water from the interior area 116 of the bottle passes directly into the end cap opening 78 in end cap 18 which is disposed vertically above the bottle bottom end 114. This may be done for example to reduce the flow restriction that would otherwise be presented by leaving the fitting 22 in position at the lower axial end of the filter. This configuration may also be desirable in certain water holding bottle configurations where the closed bottom end 114 is better suited for being disposed from the flat circular outer face of the filter rather than the fitting. Of course this approach is exemplary and other embodiments other approaches may be used.

Further it should be understood that the exemplary filter may be used with either of the fittings as the inlet or outlet. The exemplary filter thus can be used in configurations where the outlet tube 108 may be connected to either fitting. Likewise the fitting that is not in connection with the tube 108 may be used for water entering the filter, or may alternatively be disengaged from the filter and removed in some configurations to facilitate installation and flow into the filter.

Figure 9:
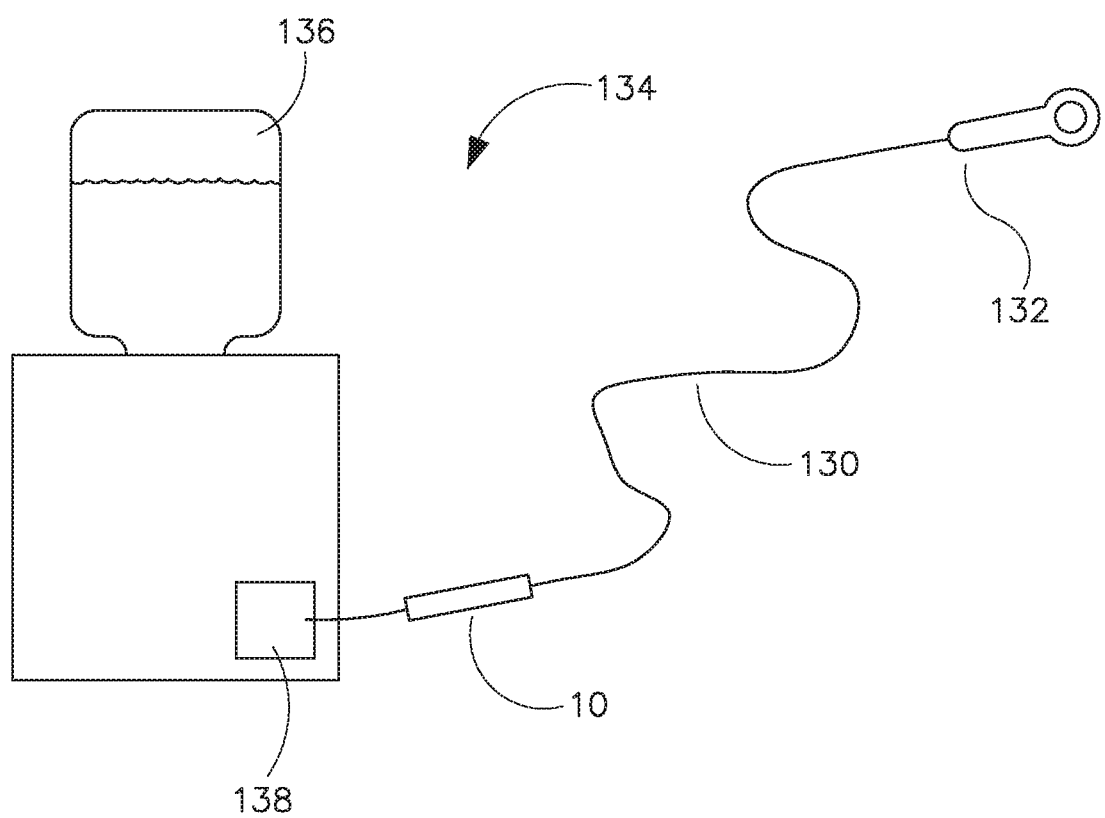
FIG. 9 is a schematic view showing an exemplary filter installed in a line which supplies water to an alternative dental instrument.

FIG. 9 shows schematically the use of an exemplary dental instrument water supply filter 10 in connection with a flexible water line referred to herein as tube 130 which supplies water to a manually engageable dental instrument 132. In the exemplary arrangement the dental instrument 132 is connected to a device schematically indicated 134. In this exemplary arrangement device 134 may comprise a scaler or air polishing device. Such devices include a water reservoir 136 which holds water for use in connection with the instrument. The exemplary device 134 further includes a pump 138 which operates to pump water through the water line tube to the instrument 132.

Figure 10:
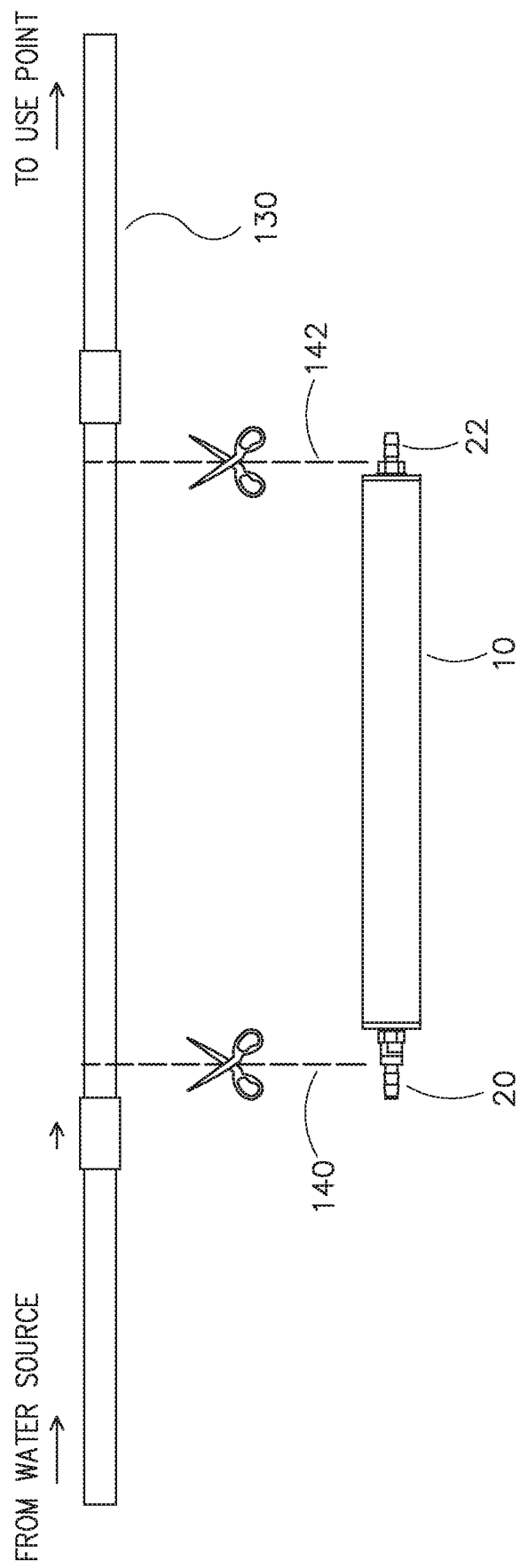
FIG. 10 is a side schematic view representing the configuration of the water supply line in which an exemplary filter may be installed.

As schematically represented in FIG. 10, the exemplary filter 10 can be installed in the water line tube by severing the tube into 2 pieces at one or more cut lines, schematically represented 140, 142. The respective fittings 20, 22 of the filter are connected in fluid tight engagement with the flexible water line tube on respective sides of the one or more cuts which sever the tube 130. With the filter 10 installed in the water line tube 130, water is enabled to flow from the reservoir 136 through the pump 138 and out of the device 134, through the tube 130 and the filter 10, to the instrument 132. In this exemplary arrangement when a water tight swivel joint is included in at least one of the fittings, movement of the instrument 132 and various rotations of the instrument and tube are accommodated by the ability of the filter 10 to rotate. This avoids twisting of the tube and/or resistance of the instrument to movement as may be desired by the user of the instrument 132. Of course it should be understood that this arrangement is exemplary and in other embodiments other approaches may be used.

It should be understood that in other exemplary arrangements the exemplary filter may be installed in other suitable locations. For example, in some devices that include a water supply reservoir, the filter may be installed in a water line that extends between the water supply reservoir and the pump that operates to pump the water to the dental instrument. Alternatively or in addition, a filter may be installed in a water line between the water supply reservoir and the pump and another filter may be installed between the pump and the dental instrument. In still other exemplary arrangements, devices that are used in connection with dental instruments may be in connection with a pipe or other water delivery conduit that provides water from a city water supply or from a filter/softener system that treats water from a well or other external supply. In such arrangements one or more filters of the exemplary embodiments may be in fluid connection between the water delivery conduit and the device that supplies the water to the dental instrument. In such arrangements the water that enters the device to which the dental instrument is connected, is filtered and treated to reduce the risk of contamination of the water lines and other components such as valves within the device, as well as in the water line to the dental instrument. Of course it should be understood that these approaches and configurations for treating water that is supplied to a dental instrument are exemplary and numerous different arrangements and configurations may be used.

Alternative exemplary embodiments may be used in connection with systems that operate to help maintain the disinfected condition of water lines, instruments and other water contacting components associated with dental instruments by assuring that the filter and microorganism growth retarding properties provided thereby are properly maintained to provide optimum performance. As can be appreciated the filters of exemplary embodiments eventually through use have their filtering and ion delivery effectiveness reduced. When the effectiveness has dropped to below a certain level, the exemplary filter requires replacement. Alternative exemplary embodiments of the dental instrument water supply filter may be used in connection with systems that operate to remind the user when the filter has been in service for a time period that corresponds to a need to replace the filter with a new filter in order to maintain assured effectiveness.

Figure 11:
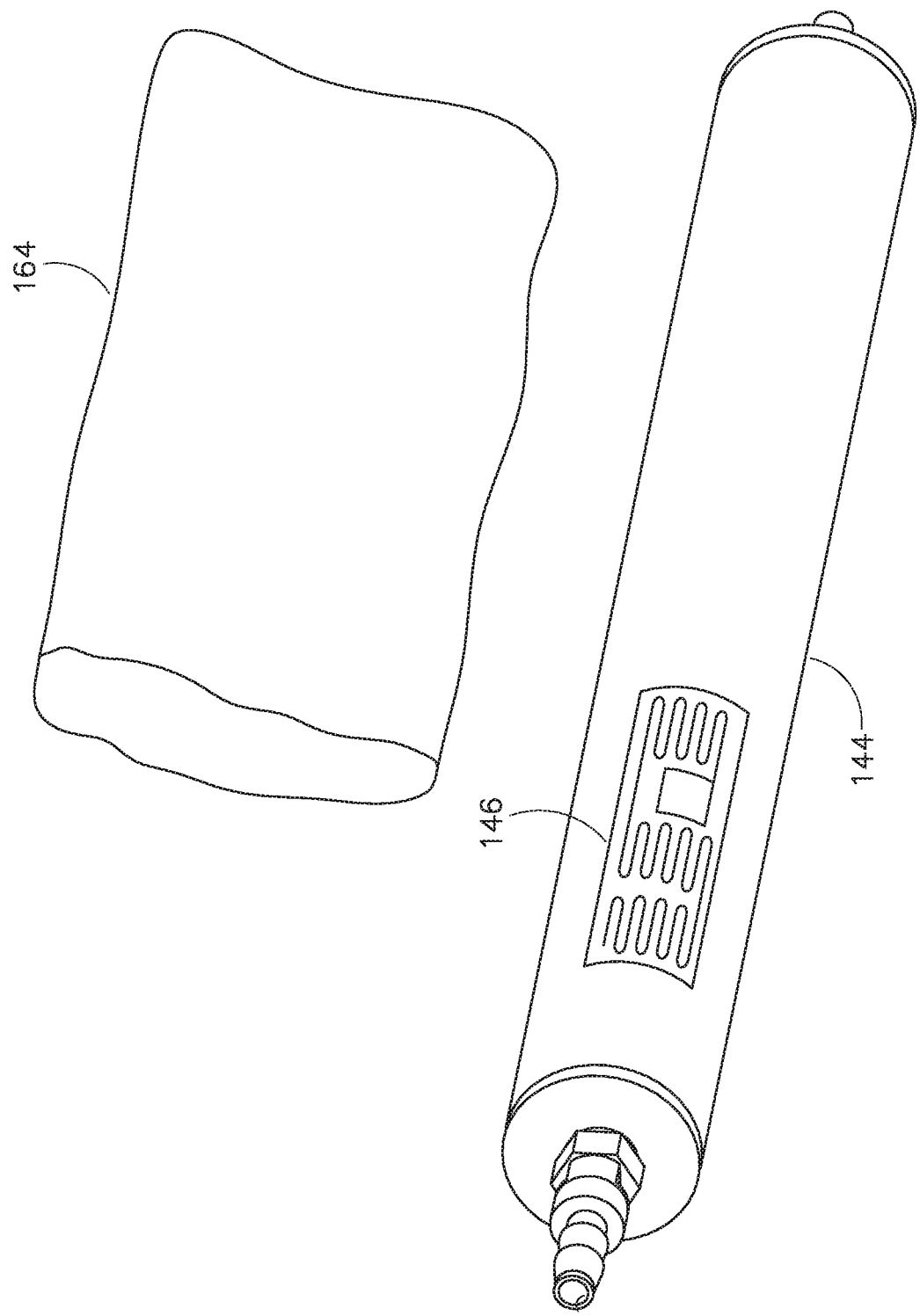
FIG. 11 is a perspective view of an alternative exemplary filter including a radio frequency identification tag, and a radio frequency insulating container in which the filter may be housed prior to installation.
Figure 12:
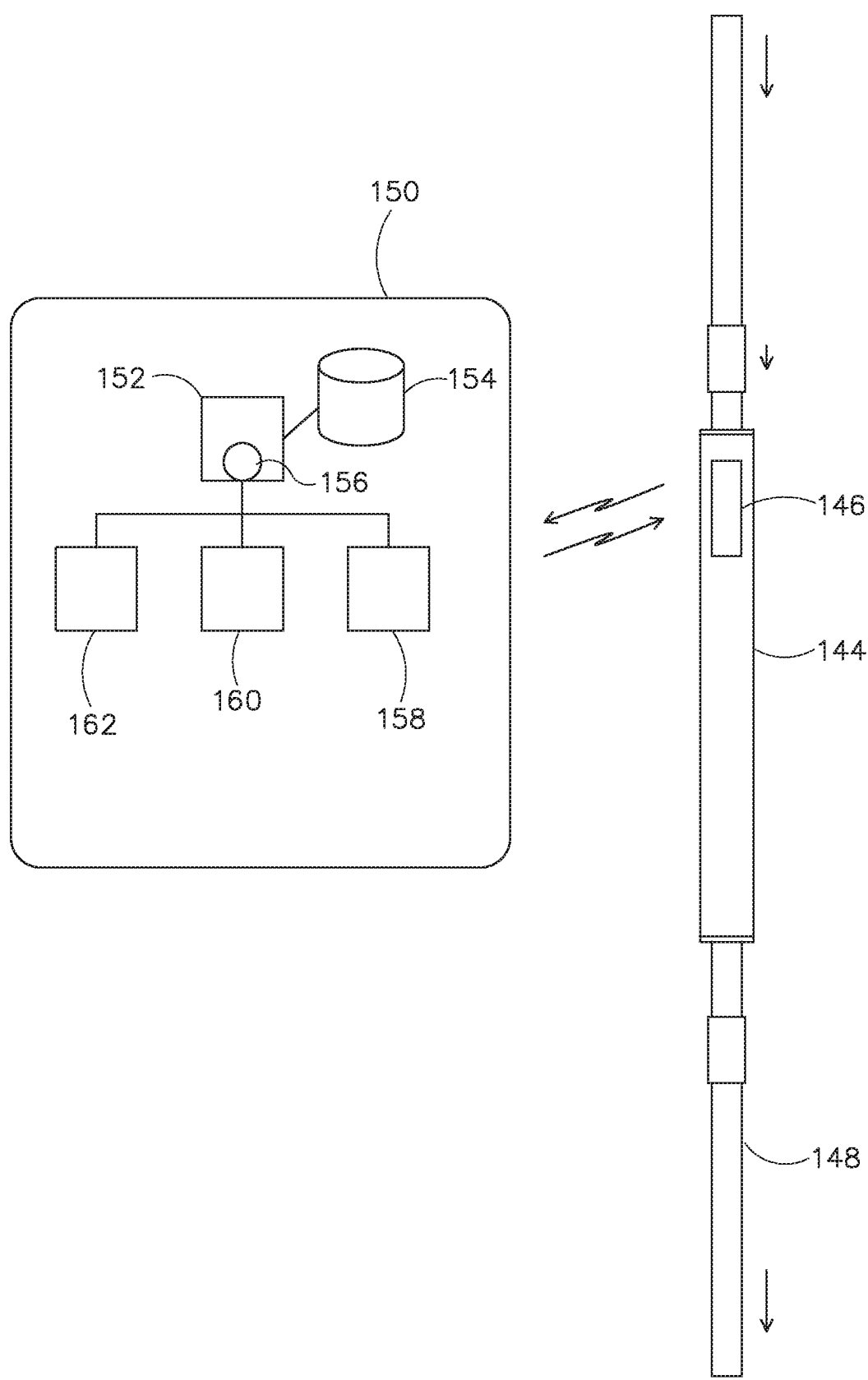
FIG. 12 is a schematic view of at least one circuit that operates to determine a time for replacement of an exemplary filter and provides an output indicative thereof.

FIG. 11 shows an alternative embodiment of a dental instrument water supply filter 144. Filter 144 may have a configuration and structure similar to filter 10 except as otherwise specifically described. The exemplary filter 144 includes a signal emitting circuit 146 that is operative to output at least one signal that includes data that specifically identifies the particular filter unit. In some exemplary arrangements the signal emitting circuit 146 associated with the filter may include a radio frequency identification (RFID) tag. The RFID tag may operate responsive to the receipt of radio frequency signals to output responsive signals that identify the particular filter unit. Of course it should be understood that the described signal emitting circuit is exemplary, and in other embodiments other arrangements may be used.

In the exemplary alternative arrangement, the filter 144 may be used in connection with a water line or other water conduit which supplies water to a dental instrument 148. The water line 148 may be one associated with a water holding bottle of the type previously discussed, a water line leading to a dental instrument from a device which includes a reservoir and a pump, or other type of water delivery conduit.

At least one circuit schematically indicated 150 is utilized in connection with the exemplary filter 144 to indicate to users that a replacement time period for the installed filter has been reached, and to provide an indication of the need to replace the filter by providing at least one output from at least one output device. In the exemplary arrangement the at least one circuit 150 includes a circuit device such as a microprocessor 152. The exemplary microprocessor is operative to execute circuit executable instructions. Microprocessor 152 is in operative connection with at least one data store 154. The exemplary microprocessor includes or is in connection with nonvolatile storage medium including instructions that provide a basic input/output system (BIOS). For example, the processor may correspond to one or more of a combination of a CPU, FPGA, ASIC or any other integrated circuit or other type of circuit that is capable of processing data and instructions. The one or more data stores may correspond to one or more of volatile or nonvolatile memories such as random-access memory, flash memory, magnetic memory, optical memory, solid-state memory or other devices that are operative to store processor executable instructions and data. Processor executable instructions may include instructions in any of the plurality of programming languages and formats including, without limitation, routines, subroutines, programs, threads of execution, objects, methodologies and functions which carry out the actions such as those described herein. Structures for processors may include, correspond to and utilize the principles described in the textbook entitled Microprocessor Architecture, Programming and Applications with the 8085 by Ramesh S. Gaonker (Prentice Hall, 2002) which is incorporated herein by reference in its entirety. Of course it should be understood that the structures are exemplary of many different types of processors and circuits that may be used.

Further it should be understood that data stores used in connection with exemplary embodiments may include one or more of several types of mediums suitable for holding non-transitory computer executable instructions. This may include for example, magnetic media, optical media, solid-state media or other types of media such as RAM, ROM, PROMs, flash memory computer hard drives or any other form of suitable media for holding data and computer executable instructions.

In the exemplary arrangement the exemplary microprocessor 152 includes a timer schematically indicated 156. In the exemplary arrangement the timer 156 includes a system clock that in connection with the associated processor circuitry and data, is operative to determine a current time as well as elapsed time information. Of course this approach is exemplary and other embodiments other types of timers may be used.

The at least one circuit 150 further includes a transceiver 158. The exemplary transceiver is configured for transmitting radio frequency signals to the signal emitting circuit 146 and for receiving signals therefrom including the filter identifying data. The at least one circuit 150 further includes at least one output device 160. The exemplary output device may include a visual output device such as a light or display. The exemplary output device may additionally or alternatively include an audible output device such as a beeper, chime or synthesized voice output device. The exemplary output device may also include a device interface such as a network interface card, chipset or other suitable device for providing wired or wireless output signals which can be received by another system or device which provides indications to users. Of course it should be understood that these output devices are merely exemplary of such devices that may be used in connection with various types of systems which have the capabilities described herein.

The exemplary circuitry further includes at least one input device 162. The at least one input device 162 may include at least one of a button, a keypad, a microphone or other audio input device, a motion sensor, contact sensor or other device which is capable of receiving selective inputs from a system user. Of course it should be understood that the components of the exemplary at least one circuit 150 are exemplary, and other circuitry and systems which carry out the functions described herein may include different or additional components.

In operation of an exemplary system, an indication is given to a system user of the need to replace the dental instrument water supply filter 144. In an exemplary arrangement prior to installation of the filter 144 in connection with the water line 148, the filter is housed in a radio frequency insulating container 164. In this exemplary arrangement the container 164 may comprise a bag, box, envelope or other suitable container that is operative to house the filter while preventing signals from the transceiver 158 or other similar transmitting device from communicating with the signal emitting circuit 146 on the filter.

Once the filter 144 has been removed from the container 164 and is installed in the water line 148, a water holding bottle or other mounting arrangement as previously discussed, the signal emitting circuitry communicates with the transceiver 158. The communication with the transceiver causes the transceiver to receive at least one signal from the circuit 146 that includes data that uniquely identifies the particular filter unit. In some exemplary arrangements this may include a particular serial number or other identifying numbers or values associated with the particular filter. In other exemplary arrangements the filter identifying data may include information such as a model number, type, performance capabilities or other data that is associated with the particular filter. In some exemplary arrangements the used filter may be placed in the container 164 for disposal, which results in the transceiver no longer receiving identifying information from the used filter.

In the exemplary arrangement the transceiver is in operative connection with the timer 156 function that is included in the microprocessor 152. The microprocessor operates in conjunction with the timer in accordance with instructions stored in the at least one data store 154, to determine when the filter identifying data is initially received by the at least one circuit 150 for the new filter. Such data may correspond to a time when the filter has been placed in service. Alternatively or in addition, the programming associated with the microprocessor may include instructions which are operative responsive to receiving new filter identifying data to prompt a user through the at least one output device 160, to provide at least one input through the at least one input device 162 indicating that the new filter has been placed in service. Of course these approaches are exemplary and other embodiments other approaches may be used.

The exemplary microprocessor operates in accordance with its associated circuit executable instructions to store in the at least one data store 154, data corresponding to a time when the filter identifying data is first received which corresponds to when the filter was placed in service. The exemplary microprocessor further operates in accordance with its programming and stored instructions in the at least one data store, to determine a replacement time for the filter after the filter has been placed in service and the use thereof commenced. In some exemplary arrangements this may include the calculation of a future date which corresponds to the useful life of the particular filter unit after which it requires replacement in order to maintain optimum water purification and disinfecting capabilities in the system.

The exemplary at least one circuit operates to determine that the replacement time period for the filter unit is reached. Responsive at least in part to this determination the at least one circuit is operative in accordance with its stored instructions to cause at least one output through the at least one output device 160. The at least one output in the exemplary arrangement is configured to indicate to a user the need for replacement of the filter 144. In exemplary arrangements the at least one output may include visual, audible and/or other types of outputs as considered appropriate to indicate to appropriate individuals the need for replacement of the particular filter unit.

It should be understood that in some exemplary arrangements the at least one circuit 150 may be operative to track and calculate concurrently the replacement times for numerous different filter units that may be in service in the dental office or other establishment in which the filters are used. Exemplary arrangements may provide outputs from displays of computing devices in operative connection with the at least one circuit 150 which inform the user of the particular filter unit which requires replacement. This may include information such as a location of the filter, the instrument associated with the filter and/or the type and model of filter which requires replacement. In some exemplary arrangements the at least one circuit 150 may be operative to compare the filter identifying data associated with a depleted filter with filter identifying data for replacement filter to verify that the replacement filter is the appropriate type of filter to be utilized in the particular device or in connection with the particular dental instrument to which the filter is operatively connected. Exemplary circuitry may operate to determine that a filter has been removed from service responsive at least in part to the wireless identifying signals from the filter no longer being received, user inputs through at least one input device, or combinations thereof. In some exemplary arrangements the programming associated with the at least one circuit may be operative to provide outputs which indicate to the user a situation in which a replacement filter that has been installed is not appropriate and/or not optimum for use in connection with the particular dental instrument.

In still other exemplary arrangements the associated at least one circuit 150 may be operative to utilize the filter identifying data to determine that a replacement filter is configured with different capabilities than a prior filter which was installed in connection with the particular dental instrument. The exemplary circuitry may be operative to determine based on the filter identifying data and data stored in the at least one data store, to determine that the replacement filter has a different useful life than the filter that it has replaced and to calculate the replacement time for the new filter in accordance with the different capabilities and useful life of the replacement filter.

Of course it should be understood that these capabilities described in connection with the exemplary system are exemplary, and in other embodiments other features, functions and capabilities may be provided to facilitate the need to replace dental instrument water supply filters that installed in a facility with which the system is associated.

Thus the exemplary embodiments described herein achieve improved operation, eliminate difficulties encountered in the use of prior devices and systems, and attain the useful results described herein.

In the foregoing description certain terms have been used for brevity, clarity and understanding. However, no unnecessary limitations are to be implied therefrom because such terms are used for descriptive purposes and are intended to be broadly construed. Moreover the descriptions and illustrations herein are by way of examples and the new and useful features are not limited to the exact features that have been shown and/or described.

It should be understood that the features and/or relationships associated with one embodiment can be combined with the features and/or relationships from another embodiment. That is, various features and/or relationships from various embodiments can be combined together, in whole or in part, in other embodiments. The inventive scope of the disclosure is not limited to only embodiments that are shown or described herein.

Having described features, discoveries and principles of the exemplary embodiments, the manner in which they are constructed and operated, and the advantages and useful results attained; the new and useful features, devices, elements, arrangements, parts, combinations, systems, equipment, operations, methods, processes and relationships are set forth in the appended claims.

What is claimed:

1. An apparatus comprising:
a dental instrument water supply filter, including
a hollow cylindrical body, wherein the body
extends along a longitudinal axis,
bounds a body interior area, and
includes a pair of opposed axial end openings,
a pair of end caps,
wherein the end caps are in fixed engagement with the body,
wherein a respective end cap closes a respective axial end opening of the body,
wherein each end cap includes an axially aligned end cap opening therethrough,
a pair of rigid water permeable discs,
wherein each disc extends within the body interior area and is in abutting relation with a respective one of the end caps,
a plurality iodinated resin particles,
wherein the plurality of iodinated resin particles are within the body interior area and intermediate of the water permeable discs,
wherein the iodinated resin particles are sized so as to not be able pass through the water permeable discs, and
a pair of fittings, wherein each fitting is configured to enable water flow therethrough,
wherein each fitting is
releasably engaged in fluid tight relation with a respective end cap opening in a respective end cap, and
is configured to be releasably engaged in fluid tight relation with a flexible water line; and
wherein each fitting includes
a threaded fitting end in releasable threaded engagement with a respective end cap opening,
a barbed fitting end opposed of the threaded fitting end, wherein the barbed fitting end is configured to be releasably engaged with the flexible water line,
wherein at least one fitting includes a fluid tight rotatable swivel joint intermediate of the threaded fitting end and the barbed fitting end.

2. The apparatus according to claim 1
wherein each end cap includes an outer face and an inner face, wherein a respective fitting extends from an outer end of the respective end cap opening on the outer face of the respective end cap,
wherein the inner face includes a recess,
wherein an inner end of the respective end cap opening in the respective end cap is within the recess and the recess extends in annular surrounding relation of the inner end of the end cap opening.

3. The apparatus according to claim 1
wherein each end cap includes an outer face and an inner face, wherein a respective fitting extends from an outer end of the respective end cap opening on the outer face of the respective end cap,
wherein the inner face includes a hemispherical recess, wherein an annular land extends in surrounding relation of the recess,
wherein an inner end of the respective end cap opening in the respective end cap is within the recess and the recess extends in annular surrounding relation of the inner end of the end cap opening, and
wherein the respective annular land is in abutting relation with a respective water permeable disc.

4. The apparatus according to claim 1
wherein each end cap includes
a generally cylindrical plug portion and an annular flange portion, wherein the annular flange portion extends radially outward relative to the plug portion,
wherein the plug portion of a respective end cap extends in the body interior area from a respective axial end opening, and the flange portion is in abutting engagement with the hollow cylindrical body outside the axial end opening.

5. The apparatus according to claim 1
wherein each end cap includes
a generally cylindrical plug portion and an annular flange portion, wherein the annular flange portion extends radially outward relative to the plug portion,
wherein the plug portion of a respective end cap extends in the body interior area from a respective axial end opening, and the flange portion is in abutting engagement with the hollow cylindrical body outside the axial end opening,
wherein the flange portion includes a flat circular outer face, and
wherein the end cap opening of the respective end cap extends through the flat circular outer face.

6. The apparatus according to claim 1
wherein each end cap includes
a generally cylindrical plug portion and an annular flange portion, wherein the annular flange portion extends radially outward relative to the plug portion,
wherein the plug portion of a respective end cap extends in the body interior area from a respective axial end opening, and the flange portion is in abutting engagement with the hollow cylindrical body outside the axial end opening,
wherein the flange portion includes a circular outer face, and
wherein the end cap opening of the respective end cap extends through the circular outer face.

7. The apparatus according to claim 1
wherein each end cap includes
a generally cylindrical plug portion and an annular flange portion, wherein the annular flange portion extends radially outward relative to the plug portion,
wherein the plug portion of a respective end cap extends in the body interior area from a respective axial end opening, and the flange portion is in abutting engagement with the hollow cylindrical body outside the axial end opening,
wherein the flange portion includes a flat circular outer face,
wherein the end cap opening of the respective end cap extends through the flat circular outer face,
wherein each fitting includes
a radially enlarged fitting portion,
wherein the threaded fitting end extends axially from the radially enlarged fitting portion,
wherein the radially enlarged fitting portion includes an annular flat fitting face that extends perpendicular to the axis, and
an annular resilient seal, wherein the seal extends in surrounding relation of an adjacent end cap opening and axially between the flat circular outer face of the end cap and the flat fitting face.

8. The apparatus according to claim 1
wherein each end cap includes
- a generally cylindrical plug portion and an annular flange portion, wherein the annular flange portion extends radially outward relative to the plug portion,
- wherein the plug portion of a respective end cap extends in the body interior area from a respective axial end opening, and the flange portion is in abutting engagement with the hollow cylindrical body outside the axial end opening,
  - wherein the flange portion includes a flat circular outer face,
  - wherein the end cap opening of the respective end cap extends through the flat circular outer face, wherein each fitting includes
- a radially enlarged fitting portion,
  - wherein the threaded fitting end extends axially from the radially enlarged fitting portion,
  - wherein the radially enlarged fitting portion includes an annular flat fitting face that extends perpendicular to the axis, and
  - a plurality of angularly disposed wrench flats, and an annular resilient seal, wherein the seal extends in surrounding relation of an adjacent end cap opening and axially between the flat circular outer face of the end cap and the flat fitting face.

9. The apparatus according to claim 1
and further comprising:
a water bottle, wherein the bottle includes a bottle interior area and has a vertically extending flexible water line in the bottle interior area,
wherein the filter extends with the axis vertically in the bottle interior area, and is supported through engagement of the fitting end of one of the pair of fittings with the flexible water line.

10. The apparatus according to claim 1
and further comprising:
a water bottle, wherein the bottle includes a bottle interior area and has a vertically extending flexible water line in the bottle interior area,
wherein the filter extends with the axis vertically in the bottle interior area, and is supported through engagement of the fitting end of one of the pair of fittings with the flexible water line, and
wherein the other of the pair of fittings is disengaged from the filter.

11. The apparatus according to claim 1
and further comprising:
a water bottle, wherein the bottle includes a bottle interior area and has a vertically extending flexible water line in the bottle interior area,
wherein the bottle includes a closed bottle bottom end that closes the interior area,
wherein the filter extends with the axis vertically in the bottle interior area, and is supported through engagement of the fitting end of one of the pair of fittings with the flexible water line,
and wherein the other of the pair of fittings is disengaged from the filter,
wherein the end cap opening from which the other of the pair fittings has been disengaged is disposed vertically above the closed bottle bottom end.

12. The apparatus according to claim 1
and further comprising
a flexible water line tube,
a dental tool fluidly connected to the water line tube,
wherein the flexible water line tube is in fluid tight engagement with at least one of the fittings.

13. The apparatus according to claim 1
and further comprising
a flexible water line tube, wherein the water line tube is severed at a cut,
a dental tool fluidly connected to the water line tube,
wherein each of the respective fittings is in fluid tight engagement with the flexible water line tube on a respective side of the cut.

14. The apparatus according to claim 1
and further comprising
an RFID tag in operative connection with the filter body,
wherein the RFID tag is operative to output at least one signal that includes filter identifying data.

15. An apparatus comprising:
a dental instrument water supply filter, including
a hollow cylindrical body, wherein the body
extends along a longitudinal axis,
bounds a body interior area, and
includes a pair of opposed axial end openings,
a pair of end caps,
wherein the end caps are in fixed engagement with the body,
wherein a respective end cap closes a respective axial end opening of the body,
wherein each end cap includes an axially aligned end cap opening therethrough,
a pair of rigid water permeable discs,
wherein each disc extends within the body interior area and is in abutting relation with a respective one of the end caps,
a plurality iodinated resin particles,
wherein the plurality of iodinated resin particles are within the body interior area and intermediate of the water permeable discs,
wherein the iodinated resin particles are sized so as to not be able pass through the water permeable discs,
a pair of fittings, wherein each fitting is configured to enable water flow therethrough,
wherein each fitting is
releasably engaged in fluid tight relation with a respective end cap opening in a respective end cap, and
is configured to be releasably engaged in fluid tight relation with a flexible water line,
an RFID tag in operative connection with the filter body,
wherein the RFID tag is operative to output at least one signal that includes filter identifying data, and
at least one circuit, wherein the at least one circuit includes
a transceiver, wherein the transceiver is operative to receive the at least one signal including the filter identifying data,
a timer,
an indicator,
at least one data store, wherein the at least one data store includes data corresponding to
the filter identifying data,
a start time when the filter identifying data was first received by the transceiver,
a replacement time period after commencing use when a filter is to be replaced,
wherein the at least one circuit is operative to
determine when the replacement time period after the start time is reached, responsive at least in part to the determination, to cause at least one output from the indicator.

16. An apparatus comprising:
a dental instrument water supply filter including:
   a hollow body, wherein the body bounds an interior body area,
   a pair of fluid fittings in releasable external engagement with the body,
   wherein each fitting includes
      a first end in releasable threaded engagement with the body,
      a second end opposed of the first end, wherein the second end is configured for releasable fluid tight engagement with a flexible water line,
   a pair of rigid water permeable pieces,
      wherein a respective water permeable piece extends fluidly intermediate between the body interior area and a respective fitting,
   a plurality of iodinated resin particles within the body interior area,
   wherein the water permeable pieces are operative to prevent the iodinated resin particles from passing out of the body interior area to the fittings, and
   wherein at least one fitting includes a fluid tight rotatable swivel joint between the first end and the second end of the respective fitting.

17. The apparatus according to claim 16
wherein the body comprises a hollow cylindrical body that extends along a longitudinal axis, wherein the body includes a pair of opposed axial end openings,
a pair of end caps, wherein each of the end caps is in fixed engagement with the body,
   wherein one respective end cap closes a respective axial end opening of the body,
   wherein each end cap includes an axially aligned end cap opening therethrough,
wherein each respective end cap opening is in releasable engagement with a respective fitting.

\* \* \* \* \*